United States Patent [19]

Mathieu et al.

[11] Patent Number: 4,551,147
[45] Date of Patent: Nov. 5, 1985

[54] APPARATUS FOR RUNNING OFF LIQUIDS FROM SEALED VESSELS

[75] Inventors: Bernd Mathieu; Wolfram Weber, both of Spiesen, Fed. Rep. of Germany

[73] Assignee: Fresenius AG, Hamburg, Fed. Rep. of Germany

[21] Appl. No.: 462,442

[22] Filed: Jan. 31, 1983

[30] Foreign Application Priority Data

Feb. 5, 1982 [DE] Fed. Rep. of Germany ....... 3203954

[51] Int. Cl.$^4$ ............................................. A61M 5/14
[52] U.S. Cl. .................................... 604/405; 210/406; 222/189
[58] Field of Search ................ 604/405, 403; 210/406, 210/416.1; 222/189

[56] References Cited

U.S. PATENT DOCUMENTS

| | | | |
|---|---|---|---|
| 2,261,037 | 10/1941 | Schwab | 604/405 |
| 2,318,637 | 5/1943 | Schwab | 604/405 |
| 2,455,645 | 12/1948 | Barton | 604/405 |
| 2,473,153 | 6/1949 | Lager | 604/405 X |
| 2,770,234 | 11/1956 | Nesset et al. | 604/405 |
| 3,456,647 | 7/1969 | Wada | 604/405 |
| 3,783,895 | 1/1974 | Weichselbaum | 604/405 X |
| 3,881,640 | 5/1975 | Noble | 604/405 X |

Primary Examiner—C. Fred Rosenbaum
Assistant Examiner—Gene B. Kartchner
Attorney, Agent, or Firm—Pravel, Gambrell, Hewitt & Kimball

[57] ABSTRACT

A universal infusion apparatus for use with sterile, sealed bottles of infusion liquid has a hydrophobic filter for stopping possible loss of liquid through the air duct, that is used for letting air into the vessel to take the place of the liquid run off therefrom. The air filter is furthermore used for stopping bacteria from the outside air being taken up into the vessel. For decreasing the degree of vacuum necessary for starting operation of the filter when there is liquid on the inside face of it so that there is no danger of the bottle collapsing, there is an air trap or storage space in which air will be kept when liquid makes its way through the air duct. Air may then be let off from the trap through an air pipe, which comes to an end a very small distance from the inside face of the filter so that only a very small degree of vacuum is needed for moving air as a bubble out of the pipe against the inner side of the filter which is then primed and will let air through at a lower degree of vacuum than would otherwise be the case.

17 Claims, 11 Drawing Figures

APPARATUS FOR RUNNING OFF LIQUIDS FROM SEALED VESSELS

BACKGROUND OF THE INVENTION

The present invention is with respect to an apparatus for running off liquids from sealed vessels, and more specially to such an apparatus for use with sterile sealed vessels, having a liquid duct for running off liquid from the vessel, an air duct for letting air into the vessel from the outside for pressure compensation within the vessel, and an air filter joined up with the air duct.

Such apparatus is used in the medical field where it is known as universal infusion apparatus. It is so designed that liquid may be run off from the vessel under all likely working conditions. When using such apparatus the place of the volume of liquid run off from the vessel is taken by air from the outside. For ruling out the chance of microbes present in the outside air from making their way into the inside of the vessel in the air which is let into the vessel to take the place of the run-off liquid, there is an air filter through which such necessary air has to go before making its way into the infusion apparatus and then on through the air duct into the inside of the vessel. This air filter furthermore has to have the function of a liquid seal, because for example in the case of pressure infusion, when there is a gage pressure in the vessel, liquid will make its way as far as the air filter, that for this reason is made of hydrophobic material stopping, because of its nature, any loss of liquid out of the infusion apparatus.

Even although for pressure-less infusion vessels are used in the case of which the place of the run-off liquid is not taken by the vessel collapsing but by taking in air from the outside, a certain degree of gage pressure is still necessary within the vessel for forming the first air bubble on the air filter and for this reason for increasing the size of the liquid surface, before the vessel is able to take up air, that is to say before the filter is "primed" or its operation started. On the other hand collapse of many of the thin-walled infusion vessels is likely even at very low degrees of vacuum, so that the intake of air has to be got going with a vacuum level, that is less than this. Seeing that the degree of vacuum is dependent on the material and pore size of the air filter, this part of the design has been taken care of by using filters designed for this purpose.

There is a shortcoming here however inasfar as such known air filters are only water-tight up to a pressure of less than 0.5 bar. This being so, universal infusion apparatus is generally designed with air filters that are liquid-tight even at gage pressures likely on pressure infusion. However, when used for pressure-free infusion, such air filters have a higher gage pressure for forming the first air bubble. On the other hand with most of the very thin-walled vessels used for pressure-free infusion collapse is likely even at a degree of vacuum that is markedly less than the vacuum needed for forming the first air bubble. Seeing that universal infusion apparatus is used not only for pressure-less infusion but furthermore for pressure infusion, there is the shortcoming with known forms of such apparatus that they are not fluid-tight enough for pressure infusion or they do not let air into thin-walled vessels early enough for stopping them collapsing.

Even although attempts have been made at taking care of this shortcoming by fitting a check valve with a ball or a rubber sealing part for the purpose of stopping infusion liquid from running back through the air filter, such a valve has the undesired property of needing a certain pressure before opening and of being dependent on the position or angle of the apparatus for its operation. Furthermore sticking of the valve in position is likely when it is used for pressure infusions or if the apparatus is not used for some time.

SHORT OUTLINE OF THE INVENTION

For these reasons one purpose or object of the present invention is that of designing an apparatus of the sort noted that will be fluid-tight when running off liquid from sealed vessels not only under pressure but furthermore under pressure-less conditions.

A still further purpose is that of designing such an apparatus that makes certain of letting air into the vessel even when the liquid therein is to be run off with or without the use of pressure.

For effecting this purpose and further objects that will become clear in the account of the invention hereinafter, in keeping with the present invention an apparatus of the sort in question is characterized in that a storage chamber is present that is separate from the air filter and which takes up air in the form of a trapped cushion when air makes its way into the air duct.

With this design one may be certain that even if the liquid gets as far as the air filter, there will be a certain amount of air, collecting in the storage chamber, present in the apparatus in keeping with the invention. In fact it has been seen, surprisingly, that the degree of vacuum needed at the start of letting air into the vessel may be very markedly lower if only some air is present at the inside of the filter. Because however, even in the case of pressure-less infusion using prior art apparatus, liquid may make its way as far as the air filter, the air, which might otherwise be responsible for this useful effect, present in the air duct of the apparatus will be simply pushed out through the filter. Using the apparatus in keeping with the invention on the other hand it is possible to take up an air cushion in the air storage chamber even if liquid is moving into the air duct, there then being an expansion of such air as the vacuum is produced, the air moving then as an air front or single air-liquid interface or as separate bubbles onto the air filter.

This being so, it is now possible for the air filter to be made of a material which keeps the apparatus of the invention in a fluid-tight condition even when a liquid is being run off therefrom under pressure, while on the other hand the vacuum in the vessel, that is under the vacuum level at which the vessel would be collapsed, is enough to make certain that air is taken up into the vessel. A still further useful effect is that not only the air filter but furthermore the storage chamber or air trap may be placed at many different positions on the apparatus of the invention so the said apparatus may be well designed and designed with a view to lowering its price.

Further details of the invention will be seen in the claims and from the account now to be given of five different working examples of the invention to be seen in the figures.

LIST OF DIFFERENT VIEWS OF THE FIGURES

FIG. 2 is view, generally on the same lines as FIG. 1, of a second example of the apparatus of the invention.

Figure 1:
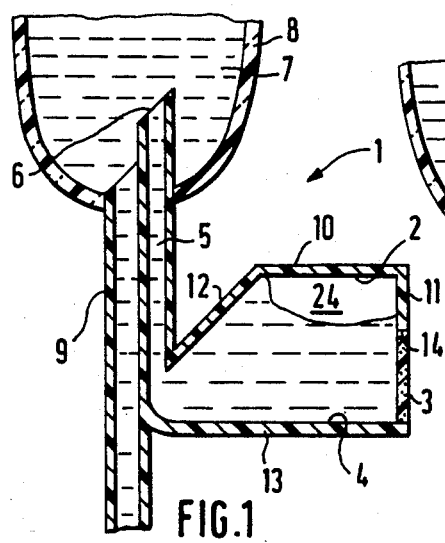
Figure 2:
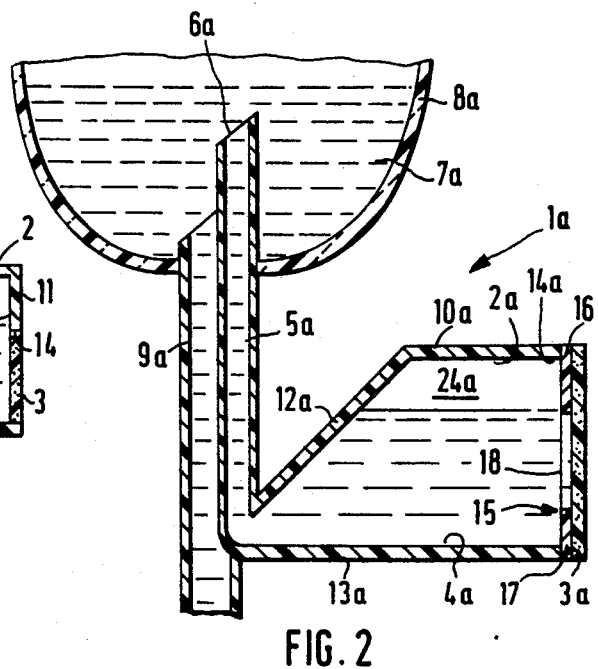
FIG. 2 is an upright section through a first working example of apparatus in keeping with the invention.
Figure 3:
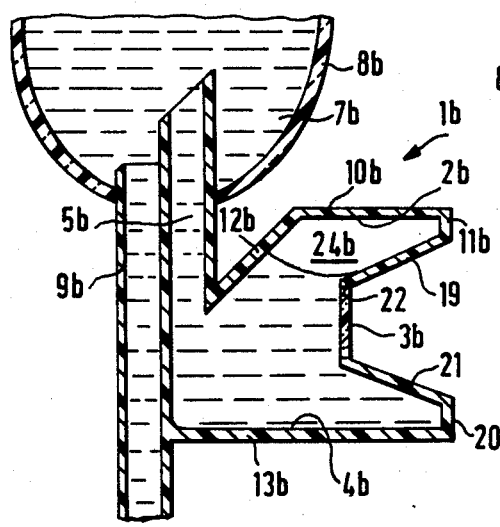
FIG. 3 is a view on the same lines as FIGS. 1 and 2 of a third working example of the invention.

FIG. 4, again on the same lines as FIGS. 1 to 3, is a view of a fourth example of the apparatus of the present invention.

Figure 4:
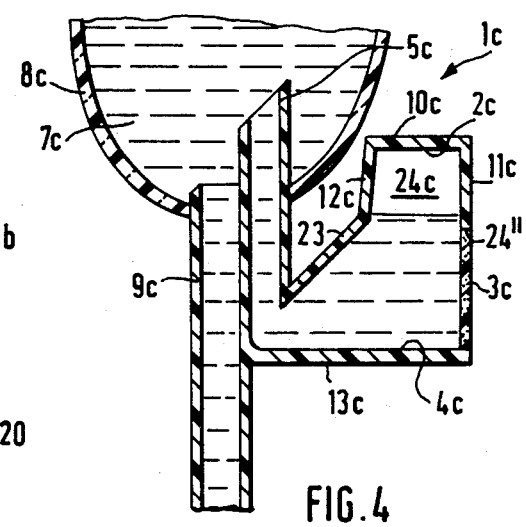
Figure 5:
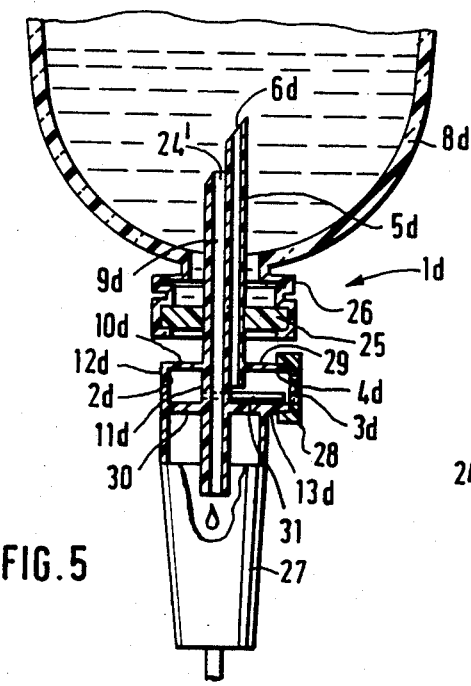

FIG. 5 is a view, generally like those of FIGS. 1 to 4, of a specially preferred example of the invention in the form of a universal infusion apparatus.

Figure 6:
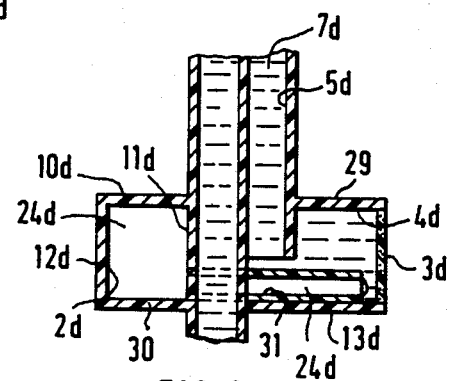
Figure 7:
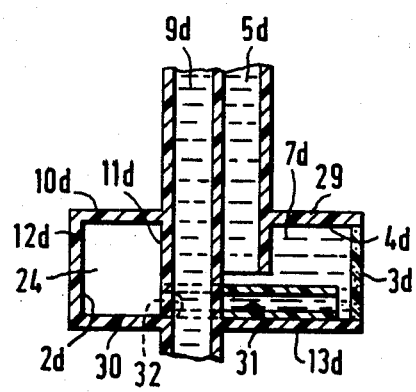
Figure 8:
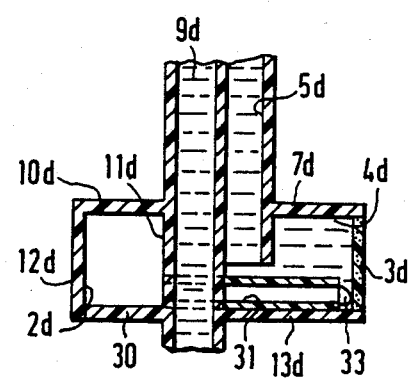

FIGS. 6 to 8 are views of part of the apparatus of FIG. 5 under different working conditions.

Figure 9:
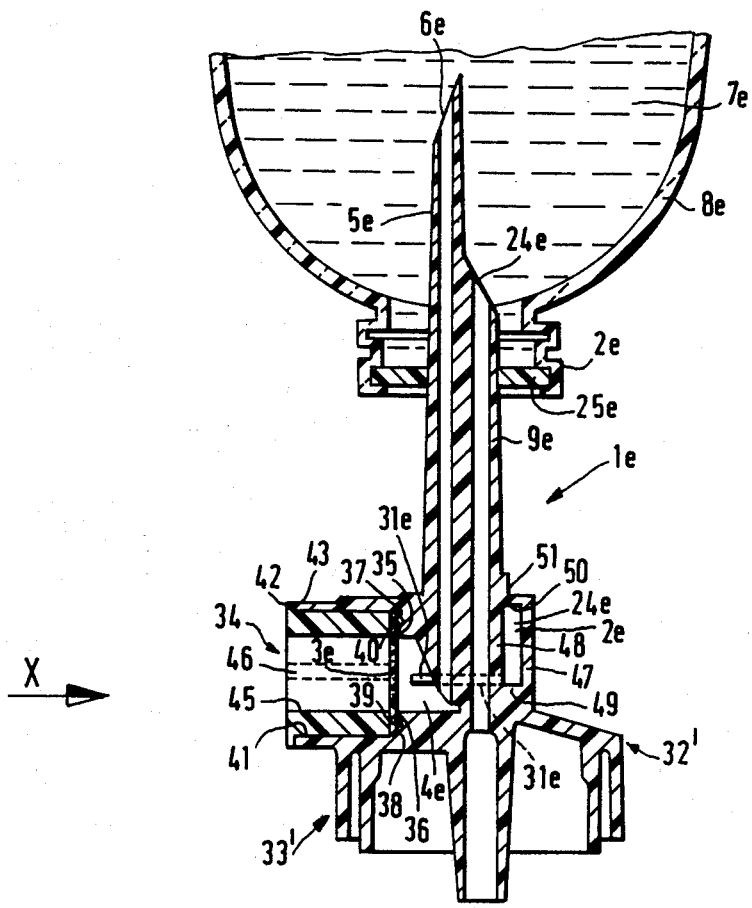

FIG. 9 is a view on the same general lines of a further specially preferred form of universal infusion apparatus in keeping with the present invention.

Figure 10:
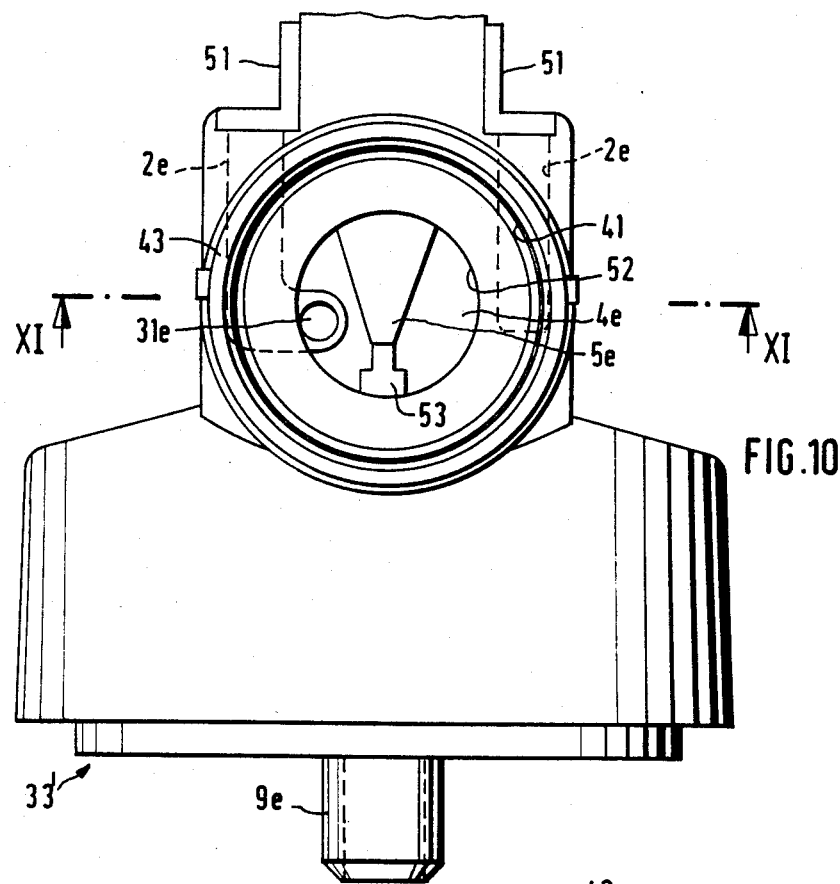

FIG. 10 is a side view on a larger scale of the example of FIG. 9 looking in the direction of the arrow X of FIG. 9.

Figure 11:
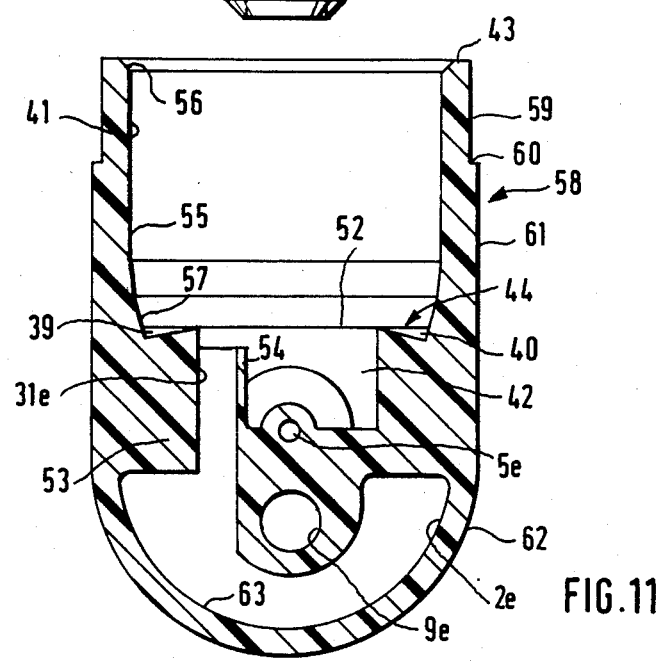

FIG. 11 is section view on a larger scale of the apparatus of FIGS. 9 and 10 taken on the line XI—XI of FIG. 10.

DETAILED ACCOUNT OF WORKING EXAMPLES OF THE INVENTION

FIGS. 1 to 4 the reader will see four working examples of an apparatus in keeping with the present invention, that are in the main only different with respect to the form of the air storage space or trap. In FIG. 1 the apparatus 1 has a trap 2 that is formed as, or is next to, the top part of a chamber 4 next to an air filter 3. The chamber 4 is joined with an air duct 5, whose end 6, that is at the top in the figure, is within a sealed vessel 8 with liquid 7 therein. Right next to the air duct 5, in the lower part of the vessel 8, there is the end opening of a liquid duct 9 for running off liquid 7 from the vessel 8. The said trap 2 or storage chamber has a top wall 10 and two side walls 11 and 12, the side wall 11 being joined with the top wall 10 at a right angle thereto and, together with a floor 13 of the chamber, forming limits of a cutout 14, in which an air filter 3 is seated and fixed, the said filter 3 being in the form of a hydrophobic diaphragm. The side wall 12 is joined at an obtuse angle with the top wall and comes to an end at the point at which the air duct 5 comes into the chamber 4. The top wall 10, the floor 13 and the side walls 11 and 12 are made air- and water-tight, whereas the air filter 3, while being water-tight, lets through air, that is to say is air-permeable or air-pervious. The side wall 11 may be formed by an air-sealing structure or masked part at the top of the air filter 3, when in place, such masking being done using coating materials. This gives the useful effect that it is only necessary for the air filter, with some changes as needed for this purpose, to be fitted to the apparatus 1 without any changes therein, and one may be certain that air will be kept trapped at 24 as a bubble.

In FIG. 2, a view of a second example of the apparatus of the invention, like parts having like part numbers with the addition of a letter a. In line with this trap of the apparatus 1a is numbered 2a and, as was the case with FIG. 1, it is next to the chamber 4a that is itself next to the air filter 3a. The air duct 5a has its ends 6a in the vessel 8a, whereas the liquid duct 9a comes to an end in the lower part of the vessel 8a.

Unlike the example of FIG. 1, the cutout 14a or window, in which the air filter 3a is placed, is limited by the top wall 10a and the floor 13a. The inside of the filter 3a is partly covered over by a ring 15 that is fixed to the top wall 10a and the floor 13a, the ring masking and covering over air-tightly the parts of the air filter 3a next to it so that it is only through an area, answering to the opening 18 of the ring 15, of the air filter 3a that air will be able to be let off from the chamber 4a. (In the figure the top and lower limits of the eedge of the ring are referenced 16 and 17.) This design is useful if rings 15 of the same size as the window 14a are on hand so that a division of the air filter 3a into parts letting through and keeping back air may be produced at a low price and without any further changes in the structure of the apparatus 1a.

The form of the invention of FIG. 3 again has its parts that are the same marked with like part numbers with the addition of a letter b. The apparatus 1b has a ring-like, annulus-like, toroidal or annular trap 2b, that is next to the top part of the chamber 4b that is next to the air fitler 3b. Furthermore the apparatus 1b has an air duct 5b and a liquid duct 9b, the same having its open end in the vessel 8b or bottle for taking in liquid 7b therefrom. The trap 2b has a round outer wall sectioned at 10b and at 13b, a side wall 12b and a further side wall on the right sectioned at 11b and 20, the side wall 12b being joined with the top of the outer wall (sectioned at 10b) at an obtuse angle and running downwards at a slope to the point at which the air duct 5b comes into the chamber. The right hand side wall sectioned at 11b and 20 is joined to the outer wall at a right angle thereto and is joined to a funnel-like or coned recurrent wall sectioned at 19 and 21, the last-named sectioned part running inwards and upwards from the said right hand side wall (as sectioned at 20) at an obtuse angle thereto. The lower part (sectioned at 20) of the upright side wall is joined with the lower part of the outer wall as sectioned at 13b. The inner end of the funnel-like wall (sectioned at 19 and 21) takes the form of a cutout or window 22 in which the air filter 3b is fitted.

The walls, sectioned at 10b, 11b, 12b and 19 and 21 of the chamber 4a and of the trap are air- and liquid-tight, whereas the air filter 3b, although water-tight, lets through air.

This third example of the apparatus is of value inasfar as it may be used at more or less any desired angle, the trap 2b or air storage chamber having in fact the form of a ring such that there is no chance of the loss of an air bubble once it is trapped therein at whatever angle the apparatus 1b is put so that it is not possible for the air to be let off through the filter 3b. .

In the further form of the invention seen in FIG. 4 like parts are marked with like part numbers with the addition this time of a letter c.

In this figure the apparatus 1c will be seen to have a trap 2c or storage chamber, that is next to the top part of the chamber 4c that for its part has the air filter 3c in its wall. The air duct 5c and the liquid duct 9c come to an end in the way noted earlier in the vessel 8c with the liquid 7c. The trap 2c is limited by the top wall 10c and the side walls 11c and 12c. In this example of the invention the side wall 12c is at a right angle to the top wall 10 c and is joined with a further wall 23 that in the figure will be seen to be running downwards at a slope to a point at which it is joined up with the wall of the air duct 5c.

The side wall 11c, that is joined at a right angle with the top wall 10c, has its edge at the limit of a cutout or window 24", that is furthermore limited by the edge of the floor 13c of the chamber 4c so that there is a dome-like form of the trap 2c, that is water- and air-tight, whereas, here as well, the filter is only water- and not air-tight. This form of the apparatus is of value if the wall 10c is to be fixed as a sort of round cover on the otherwise complete trap 2c, for example by welding or sticking.

A point common to all the four forms of the invention is that if liquid 7, 7a, 7b or 7c makes its way into the air duct 5, 5a, 5b or 5c, the air in the air duct 5, 5a, 5b or 5c will be forced partly into the chamber 4, 4a, 4b or 4c, and will be let off therefrom through the filter 3, 3a, 3b or 3c and so come out of the apparatus 1, 1a, 1b or 1c. However that part of the air is in the trap 2, 2a, 2b or 2c, will be kept here as an air cushion or bubble 24, 24a, 24b or 24c in the apparatus 1, 1a, 1b or 1c, seeing that the walls of the air trap 2, 2a, 2b or 2c do not let through any air. Because the air cushion 24, 24a, 24b or 24c is next to the air filter 3, 3a, 3b or 3c because of the design of the trap 2, 2a, 2b or 2c, if there is a vacuum in the vessel 8, 8a, 8b or 8c, expansion of the air cushion 24, 24a, 24b or 24c towards the air filter 3, 3a, 3b or 3c will be possible, this in turn priming the filter and making possible the birth of the first air bubble, as needed before air is let into the vessel 8, 8a, 8b or 8c, on the air filter 3, 3a, 3b or 3c as the case may be.

In the fifth form of the apparatus in keeping with the present invention to be seen in FIGS. 5 to 8 like parts have like part numbers, but this time with the addition of a letter d. This form of the apparatus is more specially useful as a universal infusion apparatus for pressure-less or pressure infusions.

The air duct 5d and the liquid duct 9d of the apparatus 1d are molded in one piece and have pointed, slopingly cut ends 6d and 24' like the ends of injection needles that may be used for piercing a seal part 25 fixed in the lower support part 26 of the vessel 8d that is in the form of an infusion bottle, which is sealed off thereby. The liquid duct comes to an end in the lower part of the vessel 8d and is used for running the liquid coming out of the vessel into a drip chamber 27, that is fixed on the apparatus 1d. The air duct 5d comes to an end at a point higher up than the liquid duct 9d in the vessel 8d and in the chamber 4d next to the air filter 3d. By the air filter 3d, that is in the form of a hydrophobic diaphragm, the chamber 4d is walled off from the outside, the filter being fixed by a cap 28 on the floor 13d and a top wall 29 of the chamber 4d.

In this design of the apparatus, the trap or storage chamber 2d is placed on the side of the liquid duct 9d and is walled off by the top wall 10d, the side walls 11d and 12d and a floor 30. In the present example the side wall 11d further has the function of an outer wall of the liquid duct 9d so that the trap 2d is made with the rest of the apparatus in one piece, that is to say it is integral therewith, the trap having a volume of about 50 microliters to, at the most, 1000 microliters, the preferred range being about 100 to about 200 microliters. The trap 2d is joined up with the chamber 4d at the inner side of the air filter 3d by way of an airway 31 or pipe, that has a diameter of at least about 0.3 mm, the upper diameter limit being about 3 mm, while the preferred range for the diameter of the pipe 31 is 1 to 2 mm. More specially in the case of an upright air filter 3d the airway 31, that in the present case is on the floor 13d, comes to an end a little short of the air filter 3d, that is to say with a distance of about 0.1 to 2 mm at the most therefrom, the preferred range being 0.3 to 0.8 mm.

It would furthermore be possible for the air filter 3d, that like the air filters 3, 3a, 3b or 3c is in the form of a hydrophobic diaphragm with a pore size of at least about 0.1 to 2 microns and more specially in a range of about 0.5 to 1.2 microns, to be placed in the top wall 29 in a level position, in which case it is not so important to keep to the said distances between the airway 31 and the inner face of the air filter 3d.

The workings of the apparatus 1d as viewed in FIG. 5 will now be made clear using the further FIGS. 6 to 8, that are views of a part of the apparatus 1d on a greater scale under different pressure conditions. In FIG. 6 the reader will see a condition in which, after hanging up the vessel 8d, designed as an infusion bottle and pressing on it, liquid will have been forced down through the air duct 9d as far as the air filter 3d. In this condition the liquid surface at the air filter 3d is flat or even, and energetically is at a minimum. This being so, there will be an expansion of the air cushion in the trap 2d as far as the end of the air pipe 31, it forming a liquid-air interface bulging out into the liquid a bit, without however so touching the inner face of the diaphragm 3d.

The condition seen in FIG. 7 is one produced on pressure infusion. Here the liquid 7d in the vessel 8d is under pressure and is forced by way of the air duct 5d into the chamber 4d and by then into the airway 31, the body of air 24d or air cushion being compressed in the trap 2d till it is in a balanced condition with the column of liquid. In this case the liquid 7d will go as far as a point near the end 32 of the airway 31 opening into the trap 2d.

The condition seen in FIG. 8 is one that is produced when, starting with the condition of FIG. 6, liquid has been run off from the vessel 8d by way of the liquid duct 9d. And in this case there will be a small degree of overpressure in the vessel 8d and for this reason there will be an expansion of the air cushion 24d out of the airway 31 so that a bubble 33 is produced, the same coming to rest on the inner side of the air filter 3d. In view of the small distance between the airway 31 and the inner side of the air filter 3d even a very small degree of vacuum in the vessel will be enough for causing the birth of an air bubble 33 touching the inner side of the air filter 3d. Seeing that this is so, the air filter 3d may be made of a material that on pressure infusion as in FIG. 7 makes certain that the universal infusion apparatus is fluid tight, while nevertheless making certain that air is let into the vessel 8d, because even the gage pressure produced on letting off some microliters of liquid will be great enough for the first air bubble to be produced on the inner side of the air filter 3d, this in turn stopping a collapse of the vessel 8d.

Under gage pressure conditions as for example when making a pressure infusion, the air in the trap 2d is compressed, the trap being partly filled with liquid 7d. On the pressure going down to normal, there is expansion of the air, the liquid 7d being moved out of the trap 2d. In this connection it is best for the inlet and outlet of the trap 2d or storage chamber, that is to say the airway 31, to be placed at the lowest point of the trap 2d. In view of the surface tension of the liquid 7d and the fact that the resin material of which the apparatus is made, is only wetted to a limited degree, this form of the apparatus may be positioned and used over a large range of different angles, because the liquid 7d is present in a drop form in the trap 2d and there is at all times a connection with the inside of the chamber 4d. This being so, the air is compressed and it is always the liquid 7d that is first forced out of the trap 2d, before the air is able to come out of it.

In FIG. 9 the reader will see the sixth form of apparatus of the invention, in which like parts are marked with like part numbers but with the addition of the letter e.

On the same general lines as in the apparatus of FIG. 5 the apparatus 1e has the air duct 5e and the liquid duct 9e, which are molded together as a single body and have pointed end parts so that they may be pierced like an injection needle through a sealing part 25e, that is seated in a support neck 26e or part of the vessel 8e that is in the form of an infusion bottle, for sealing the lower end thereof. The liquid duct comes to an end in the lower part of the vessel 8e so that by way of it liquid may be run off into drip chamber that is not figured, and which may be kept in place by two skirts 32' and 33' on the apparatus 1e. The open end of the air duct 5e is higher up than the liquid duct 9e in the vessel 8e and comes to an end in the chamber 4e next to the air filter 3e. The air filter 3e, that is in the form of a hydrophobic diaphragm, has the function of a liquid seal shutting off the chamber 4e from the outside and keeping back liquid that has run into the chamber 4e while at the same time acting as a bacterial filter in the opposite direction for air coming from the outside into the chamber. In the case of the present example the air filter 3e is kept in place by a stopper-like keeper part 34 against a ring-like edge that will be most clearly seen in FIG. 11 and which is sectioned at two points 35 and 36 in FIG. 9, such edge being conical on its two sides to take the form of a sealing lip biting into the filter 3e. Radially outside the edge there is conical well which is sectioned at two points 37 and 38 in FIG. 9 and at two further points 39 and 40 in FIG. 11 such well having a v-like radial section. Acted on by the part 34, the filter 3e is pressed against the said edge and into the well radially outside it, the edge biting into the filter material somewhat to make a fluid-tight joint with no chance of the filter slipping out of place.

The keeper part 34 is in the form of cylindrical stopper with a ring-like cross section. It is placed in a cylindrical space 41, whose inner diameter and length are equal to the outer diameter and length of the keeper 34. To keep the air filter 3e in place in the apparatus 1e the keeper part 34 is so placed in the space 41 that the air filter 3e is pressed thereby against the edge, that is to be seen sectioned at 35 and 36 in FIG. 9. To make certain that the keeper part 34 keeps to a given position in the space 41 it has a ring-like lip 42 or shoulder at the left end thereof which is jointed to the left end face 43 of the wall round the space 41, such joint being for example by adhesive placed between the face 43 and the lip 42. The keeper part 34 has a hole 45 therethrough in which a cross-like inner part 46 is seated permanently, it running along the full length of the keeper part 34 and acting as a safeguard for the air filter 3e In the hole 45 in the keeper 34 it is furthermore possible to have a stopper of air-tight material for covering over the air filter 3e partly or fully and stopping the flow of air therethrough if this is necessary or desired.

The trap 2e is in the instant case in the form of a space like part of a ring stretching through 180 deg. about the axis of the apparatus 1e so as to be like a half-moon or crescent. In FIG. 9 the trap 2e will be seen to be walled in by side walls 47 and 48 and a floor 49 and it has an opening 50 that in FIG. 10 will be seen to be pointing upwards and which may be shut off by way of a cover 51 that is put on after the apparatus has been molded. In the present case the cover 51 has an L-like cross section and may be fixed in place by adhesive or welding to take an example. The airway 31e comes out of the trap at the level of the floor 49 and comes to an end a small distance short of the air filter 3e in the chamber 4e on the inner side of the air filter 3e.

FIG. 10 is a side view of the apparatus 1e of FIG. 9 on a larger scale and seen looking in the direction of the arrow X, without the keeper part 34 and the air filter to make the figure more straightforward.

The space 41, that in the present example of the invention, is cylindrical and has a smaller cross section at its inner end (see FIG. 11) in the form of a round space 52 at this position in front of which the air filter 3e is placed and kept in position by the keeper part 4 as in FIG. 9. The space 52 is a connection between the space 41 and the chamber 4e on the inner side of the air filter, such chamber 4e having the air duct 5e opening into it at 52. The trap 2e or storage chamber, that is not to be seen in FIG. 10, is marked however in outline here by broken lines. The airway 31e, that is joined with the trap 2e, will be seen in ths figure to be opening to the left of the air duct 5e. It would furthermore be possible for the airway 31e to come in from the right into the chamber 4e; in the two possible designs the airway 31e is not joined with the air duct 5e or with the liquid duct 9e.

In the section of FIG. 11, that again has been made without the part 34 and the air filter 3e in place to make the figure more straightforward, the form of the trap 2e as half a ring will be noted, it stretching for 180 deg. round the liquid duct 9e. The airway 31e joining the chamber 4e and the trap 2e is in the present case walled in by an outer wall 53 of the housing and a thinner wall part 54 opposite thereto, that in the said figure is on the inner side. This being so, the airway 31e is not joined with the air duct 5e or with the liquid duct 9e. In the FIG. 11 the reader will furthermore see the ring-like well sectioned at 30, 40 and 44, noted earlier in connection with FIG. 9, that is designed to take up the air filter 3a in the way earlier noted.

The space 41 has a cylindrical inner face 55 having at one end the outer frusto-conical face 56 next to the end face 43 and at its other end a frusto-conical face 57 next to the side well, that is sectioned at 40 in this figure. An outer wall face 58 has a wall part 59, running from the end face 43 to a step 60 and then running round the back of the trap 2e in the form of the outer face 62 of the wall 47, said face 62 having by the nature of things a greater diameter than the inner face 63 of the wall 47 to which it is parallel.

The sixth form of the invention, that is more specially of value inasfar as it takes up little space while at the same time functioning quite as well in the respects noted as, more specially, the fifth form of the invention of FIGS. 5 to 8. With respect to the size of the airway 31e and its distance from the air filter 3e, the size of the trap 2e or storage chamber and the design of the air filter details may be as taken from account of FIGS. 5 to 8 of the fifth form of the invention.

We claim:

1. An apparatus for running off a liquid from a sealed vessel containing said liquid during both vacuum and pressure conditions within said vessel comprising:
a liquid duct communicating with the inside of said vessel for discharging said liquid from said vessel to its outside;
an air duct communicating on one end with the inside of said vessel and on the other end in communication with the atmosphere via an air filter means for introducing air into said vessel to equalize the pressure within said vessel with the atmosphere during the discharge of liquid from said vessel; wherein a space is disposed in said air duct in a location adjacent said air filter means being characterized in that said space is arranged as an air storage chamber or air trap which retains a body of air adjacent said air filter means even during pressurized conditions within said vessel when liquid is forced to said air duct by pressure within said sealed vessel and retained therein by said air filter means and wherein said body of air decreases the vacuum necessary to initiate air flow through said air filter means by expanding to contact said air filter means upon creation of vacuum conditions within said vessel.

2. The apparatus of claim 1 wherein said air duct comprises an air pipe ending a small distance short of said air filter means.

3. The apparatus of claim 3, wherein said air filter means is vertical during running off of liquid from said sealed vessel.

4. The apparatus of claim 3 wherein said air pipe has a diameter of from about 0.3 to about 3 mm.

5. The apparatus of claim 4 wherein said range is from about 1 to about 2 mm.

6. The apparatus of claim 2 wherein said air pipe comes to an end at a distance from said air filter means, said distance being from about 0.1 to about 2 mm.

7. The apparatus of claim 6 wherein said range is from about 0.3 to about 0.8 mm.

8. The apparatus of claim 1 wherein said air filter means comprises a hydrophobic diaphragm having a pore size in a range of from about 0.1 to about 2 microns.

9. The apparatus of claim 8 wherein said range is from about 0.5 to about 1.2 microns.

10. The apparatus of claim 1 wherein said air storage chamber of said air trap is an integral part of said apparatus, said air trap having a volume in a range of from about 50 to about 1000 microliters.

11. The apparatus of claim 10 wherein said range is from about 100 to about 200 microliters.

12. The apparatus of claim 1 wherein said air filter means is partly air-tightly masked by a coating.

13. The apparatus of claim 1 wherein said air storage chamber in said air duct is a dome-like space provided in a liquid storage chamber connecting said air filter means and said air duct.

14. The apparatus of claim 1 wherein a guard cover is provided on the outer face of said air filter means for safeguarding it from damage.

15. The apparatus of claim 1 having a separate cover walling in part of the air trap space.

16. The apparatus of claim 1 further including a ring-like lip and means for maintaining said air filter means in contact with said lip.

17. The apparatus of claim 1 in the form of a universal infusion apparatus.

* * * * *